(12) United States Patent
Green et al.

(10) Patent No.: US 10,564,124 B2
(45) Date of Patent: Feb. 18, 2020

(54) CONTROLLING GAS-PHASE ION INTERACTIONS

(71) Applicant: Micromass UK Limited, Wilmslow (GB)

(72) Inventors: Martin Raymond Green, Bowdon (GB); Jason Lee Wildgoose, Stockport (GB)

(73) Assignee: Micromass UK Limited, Wilmslow (GB)

(*) Notice: Subject to any disclaimer, the term of this patent is extended or adjusted under 35 U.S.C. 154(b) by 0 days.

(21) Appl. No.: 15/318,271

(22) PCT Filed: May 29, 2015

(86) PCT No.: PCT/GB2015/000184
§ 371 (c)(1),
(2) Date: Dec. 12, 2016

(87) PCT Pub. No.: WO2015/189552
PCT Pub. Date: Dec. 17, 2015

(65) Prior Publication Data
US 2017/0122907 A1 May 4, 2017

(30) Foreign Application Priority Data

Jun. 13, 2014 (EP) .................................... 14172335
Jun. 13, 2014 (GB) .................................. 1410580.3

(51) Int. Cl.
*G01N 27/62* (2006.01)
*H01J 49/00* (2006.01)
(Continued)

(52) U.S. Cl.
CPC ........ *G01N 27/624* (2013.01); *H01J 49/0031* (2013.01); *H01J 49/0422* (2013.01); *H01J 49/421* (2013.01)

(58) Field of Classification Search
None
See application file for complete search history.

(56) References Cited

U.S. PATENT DOCUMENTS 6,003,389 A 12/1999 Flagan et al.
6,586,732 B2 7/2003 Lee et al.
(Continued)

FOREIGN PATENT DOCUMENTS

GB 2529924 A 3/2016
WO 2013/171495 11/2013
(Continued)

OTHER PUBLICATIONS

Blagojevic, V et al., "*Differential Mobility Spectrometry of Isomeric Protonated Dipeptides: Modifier and Field Effects on Ion Mobility and Stability*", Analytical Chemistry, vol. 83, pp. 3470-3476 (Apr. 2011).

*Primary Examiner* — Andrew Smyth

(57) ABSTRACT

A mass spectrometer or ion mobility spectrometer is disclosed comprising: a first device for separating ions or molecules according to a physicochemical property; an ion mobility separation device for receiving and separating at least some of said ions or ions derived from said molecules according to their ion mobility; a gas supply connected to said ion mobility separation device for supplying gas into said ion mobility separation device; and a control system configured to adjust said gas supply so as to change the composition of gas within the ion mobility separation device as a function of time.

12 Claims, 1 Drawing Sheet

(51) Int. Cl.
    *H01J 49/04*     (2006.01)
    *H01J 49/42*     (2006.01)

(56) References Cited

U.S. PATENT DOCUMENTS

| | | | |
|---|---|---|---|
| 7,170,053 B2* | 1/2007 | Shvartsburg | G01N 27/624 |
| | | | 250/282 |
| 7,355,170 B2* | 4/2008 | Miller | G01N 27/622 |
| | | | 250/281 |
| 7,714,282 B2 | 5/2010 | Guevremont et al. | |
| 7,718,960 B2 | 5/2010 | Hashimoto et al. | |
| 9,188,565 B2 | 11/2015 | Glish et al. | |
| 2005/0127289 A1* | 6/2005 | Fuhrer | H01J 49/025 |
| | | | 250/288 |
| 2010/0108877 A1* | 5/2010 | Wu | G01N 27/622 |
| | | | 250/282 |
| 2012/0018629 A1* | 1/2012 | Eikel | G01N 1/405 |
| | | | 250/282 |
| 2013/0068946 A1* | 3/2013 | Moskovets | G01N 30/7233 |
| | | | 250/288 |
| 2013/0320205 A1* | 12/2013 | Glish | G01N 27/624 |
| | | | 250/283 |

FOREIGN PATENT DOCUMENTS

| | | |
|---|---|---|
| WO | 2015/025008 A1 | 2/2015 |
| WO | 2015/136264 | 9/2015 |

* cited by examiner

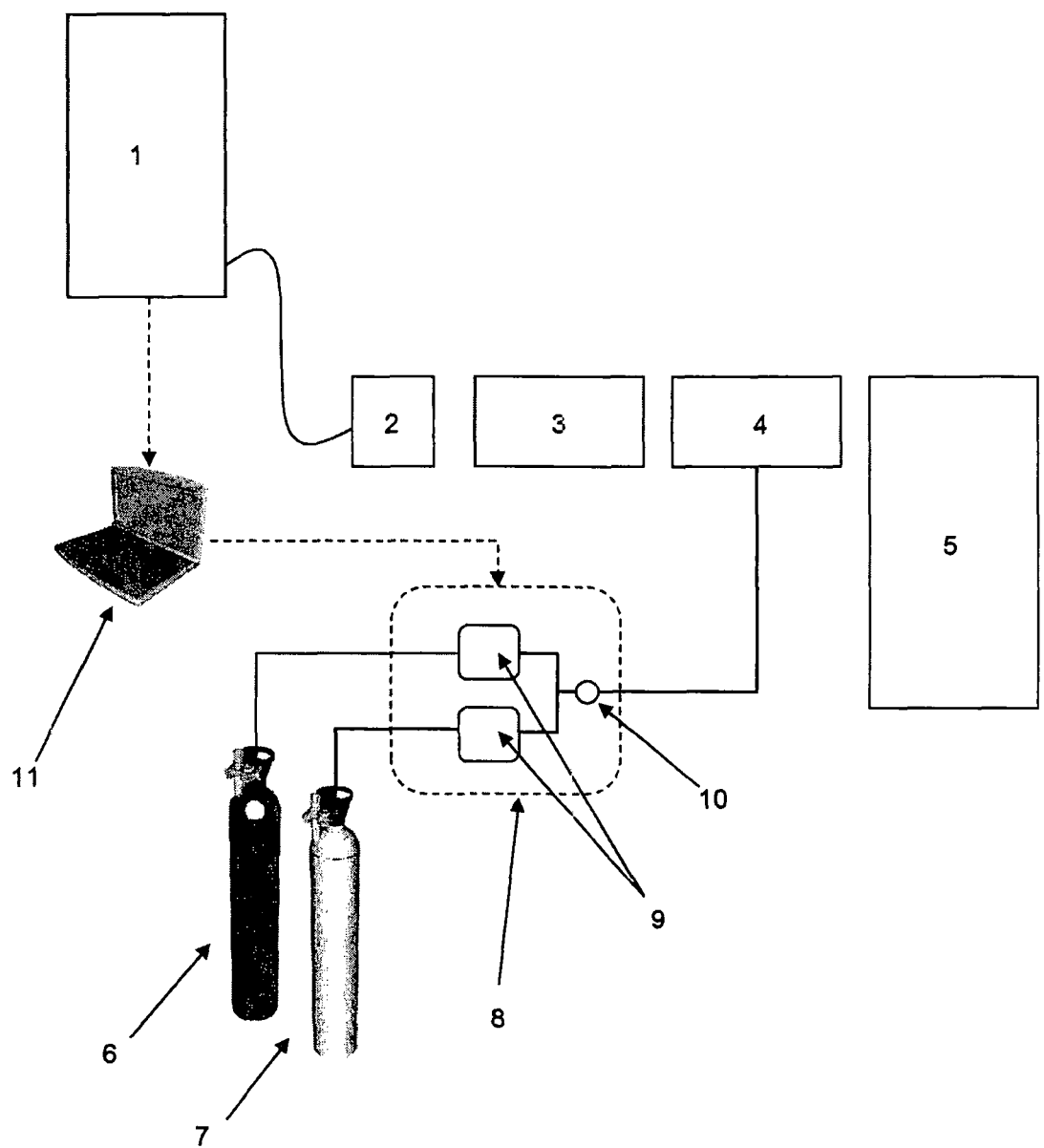

CONTROLLING GAS-PHASE ION
INTERACTIONS

CROSS-REFERENCE TO RELATED
APPLICATIONS

This application represents the U.S. National Phase of International Application number PCT/GB2015/000184 entitled "Controlling Gas-Phase Ion Interactions" filed 29 May 2015, which claims priority from and the benefit of United Kingdom patent application No. 1410580.3 filed on 13 Jun. 2014 and European patent application No. 14172335.3 filed on 13 Jun. 2014. The entire contents of these applications are incorporated herein by reference.

BACKGROUND TO THE PRESENT
INVENTION

The present invention relates to a mass or ion mobility spectrometer and a method of performing mass or ion mobility spectrometry. Embodiments of the present invention relate to a mass spectrometer or method of performing mass spectrometry employing ion mobility separation ("IMS").

In conventional targeted mass spectrometry or tandem mass spectrometry experiments such as selected ion recording ("SIR") or multiple reaction monitoring ("MRM") the presence of known target analytes are confirmed during the course of a chromatographic separation by monitoring characteristic mass to charge ratio values. IMS separation is often used to add an extra degree of selectivity to these experiments.

Ions may be separated according to their ion mobility by virtue of their different interactions with a buffer gas under the influence of an applied electric field. The nature of the interaction between the analyte ions and the gas determines the collision cross-section and hence the measured drift time of ions through an IMS device.

Ions undergo similar interactions with the buffer gas in differential ion mobility separation ("DMS") or field-assisted ion mobility separation ("FAIMS") devices. Ions also interact with the background gas in other gas-filled devices such as proton transfer reaction ("PTR") devices.

It is desired to provide an improved spectrometer and improved methods of spectrometry.

In particular, it is desired to be able to optimize the conditions within such gas-filled devices for multiple targeted ions during the course of an experiment.

SUMMARY OF THE PRESENT INVENTION

From a first aspect the present invention provides a mass spectrometer or ion mobility spectrometer comprising:
a first device for separating ions or molecules according to a physicochemical property;
an ion mobility separation or filter device for receiving and separating or filtering at least some of said ions, or ions derived from said molecules, according to their ion mobility;
a gas supply connected to said ion mobility separation or filter device for supplying gas into said ion mobility separation or filter device; and
a control system configured to adjust said gas supply so as to change the composition of gas within the ion mobility separation or filter device as a function of time.

The composition of gas within the ion mobility separation or filter device (IMS device) is changed as a function of time such that the ion mobility separation (IMS) conditions can be optimized for multiple different analyte ions eluting from the first device. For instance, optimal IMS conditions may be chosen by selecting gas compositions that achieve the best separation of analyte ions of interest from matrix ions or from other analyte ions within a sample. Dynamically varying or optimizing the IMS conditions (i.e. the gas composition in the IMS device) in this way during the course of a single experiment or separation allows the resolution of the spectrometer and its detection and quantification limits to be improved. Conventionally, the composition of the buffer gas in an IMS device is maintained static during the course of an experiment, which provides a compromise between the optimum IMS conditions for the analyte ions of interest.

US 2013/0320205 discloses a FAIMS device in which the compensation voltage is scanned in order to analyse the field asymmetric ion mobility of the ions passing therethrough. The gas composition in the device may be varied as a function of the compensation voltage in order to optimise the analysis. However, US '205 does not disclose a separator or filter upstream of the FAIMS device for separating or filtering ions or molecules according to a physicochemical property. As such, ions having different values of the physicochemical property arrive at the analyser at the same time, rather than at different times. The gas composition in the device of US '205 can therefore only be optimised for a relatively small proportion of the analyte ions passing through the analyser at any given time.

According to the present invention, the gas composition may be varied in a manner whereby the proportions of two or more different types of gases present are varied with time, either by being varied continuously or discontinuously. Alternatively, only a single type of gas may be present and the type of gas is changed with time.

The gas pressure within the IMS device may be varied continuously or discontinuously with time. Alternatively, the gas pressure may be maintained constant.

The gas pressure within the IMS device may be substantially at atmospheric pressure or may be below atmospheric pressure.

The ion mobility separation or filter device may comprise any device suitable for separating or filtering ions according to their ion mobility including drift-time or travelling wave ion mobility separation devices.

The ion mobility separation or filter device may separate ions according to their mobility through the gas composition in the device.

The ion mobility separation or filter device may be configured to drive ions of different ion mobility from an entrance of the device towards an exit of the device at different rates so as to separate or filter ions according to their drift time along or through the device.

The ion mobilities of the ions may be determined from their drift times through the device.

Accordingly, the ion mobility separation or filter device may not be a FAIMS device. However, it is contemplated that the ion mobility separation device may comprise a differential ion mobility separation device or a field-assisted ion mobility separation ("FAIMS") device in which ions are separated or filtered according to their differential ion mobility (i.e. rate of change of ion mobility with electric field strength).

A mass analyser and/or ion detector may be disposed downstream of the ion mobility separation or filter device. The mass analyser is preferably a TOF mass analyser such as an orthogonal TOF mass analyser, although other types of mass analyser may be used.

If the first device separates molecules from an analyte sample, rather than separating ions, then the spectrometer comprises an ioniser for ionising the molecules after they elute from the first device, so as to provide said ions derived from said molecules. Alternatively, the spectrometer may comprise an ion source arranged upstream of the first device for ionising an analyte sample and providing ions to said first device for separation according to said physicochemical property.

The first device may also be connected to the or a gas supply and the control system may be configured to adjust the composition of gas in the first device as a function of time. The composition of gas within the first device may be changed simultaneously with the change of gas composition within the ion mobility separation device. For instance, the first device may also be an ion mobility separation device for separating or filtering ions according to their ion mobility or different ion mobility and gas composition.

The control system may be configured to vary the gas composition in said ion mobility separation or filter device dynamically based on the separation or elution time in said first device.

The instrument of US 2013/0320205 does not vary the gas composition based on a separation or elution time of ions or molecules from an upstream device. Rather, it seems that the instrument in US '205 simply scans the gas composition with the compensation voltage so that optimal analysis conditions are provided for a portion of the ions passing through the FAIMS device at any given time. This instrument is therefore only capable of optimising conditions for a proportion of the ions passing through the FAIMS device at any given time.

The gas composition in the ion mobility separation or filter device is controlled based on the (type of) ions or molecules eluting from the first device and passing into the ion mobility separation or filter device so that the gas in the ion mobility separation or filter device is controlled to be of a first composition whilst a first analyte ion is passing through the ion mobility separation or filter device, and the gas in the ion mobility separation or filter device may be controlled to be of a second composition whilst a second, different analyte ion is passing through the ion mobility separation or filter device.

The gas composition may be changed any number of times for any number of analytes.

The composition of gas within the ion mobility separation device may be changed so as to control ion mobility separation for multiple different analyte ions, said multiple different analyte ions being targeted according to the separation in said first device.

The gas supply may comprise a plurality of gas flow controllers each connected to a reservoir of a different type of gas and said control system may be configured to control the gas flow controllers so as to change the composition of gas within the ion mobility separation or filter device as a function of time.

The first device may separate ions or molecules according to: (i) chromatographic or electrophoretic retention time; (ii) mass or mass to charge ratio; (iii) ion mobility or differential ion mobility; or (iv) volatility.

The first device may comprise: (i) a liquid chromatography device; (ii) a gas chromatography device; (iii) a super-critical fluid chromatography device; (iv) a size-exclusion chromatography device; (v) a capillary electrophoresis device; (vi) an ion trap with mass selective ejection; (vii) an ion mobility separator; (viii) a differential ion mobility separator; or (ix) a distillation device comprising a heated solids probe.

The control system may be configured to vary the gas composition in the ion mobility separation or filter device according to a set program.

The gas composition may be varied according to a predetermined program so that it can be varied reproducibly between different experiments or separations. The control system may be configured to start varying the gas composition according to a set program synchronously with the start of a separation within the first device. The control system may comprise a computer connected to both the gas supply and the first device.

The control system may be configured to adjust the composition of gas in the ion mobility separation or filter device with time so as to enhance or optimise ion mobility separation for multiple predetermined target ions present in said ion mobility separation or filter device at different times.

The enhanced or optimum gas composition for a particular analyte ion may be predetermined in advance of the experiment or separation, for example, by analysing standards of the target analytes or by performing a pre-scan in which the conditions are rapidly changed.

The spectrometer may comprise a control system configured to perform a pre-scan in which a sample comprising a plurality of target analyte ions is analysed by said ion mobility separation or filter device with different gas compositions and to determine the optimum or desired gas composition for separating or filtering the target ions in said ion mobility separation or filtering device. The control system is configured to determine the different optimum or desired gas compositions for different target ions. The control system is configured to subsequently supply a sample to said ion mobility or filter device and to perform the step of separating or filtering the ions according to their ion mobility. The control system is configured to control the gas supply such that whilst a first target ion is entering and/or separating in the ion mobility separation or filtering device the optimum or desired gas composition for the first target ion is present within the device, and whilst a second target ion is entering and/or separating in the ion mobility separation or filtering device the optimum or desired gas composition for the second target ion is present within the device.

The spectrometer may further comprise a control system configured to:

perform a pre-scan that: a) determines the elution times from the first device of a plurality of target ions, or determines the elution times from the first device of a plurality of molecules from which target ions are generated and then ionises the molecules to form target ions, and b) determines different optimum or desired gas compositions for separating or filtering different ones of the target ions in said ion mobility separation or filtering device; and then supply a sample to said first device and to perform said step of separating ions or molecules according to said physicochemical property and said step of separating or filtering said ions according to their ion mobility; and to vary the gas composition in the ion mobility separation or filter device as a function of elution time from the first device such that at elution times corresponding to the elution times of the target ions, or corresponding to the elution times of the molecules from which the target ions are generated, the gas composition in the ion mobility separation or filter device has the respective optimum or desired gas compositions for those target ions.

Different target ions are determined to have different elution times and different optimum or desired gas compositions Step b) of the pre-scan may comprise:

(i) separating or filtering the target ions according to their ion mobility in the ion mobility separation or filter device;

(ii) detecting the target ions to provide a detection signal;

(iii) repeatedly performing steps (i) to (ii), wherein the gas composition in the ion mobility separation or filter device is different for each time that step (i) is repeated; and (iv) determining the optimum or desired gas composition for each target ion as the gas composition that provides the optimum or desired signal for that target ion from the detection signals detected in step (ii). For example, the gas composition that provides the best resolution in step (ii) for a target ion may be determined to be the optimum or desired gas composition for that target ion.

The pre-scan may comprise determining the elution times of the target ions or target molecules in one scan and determining the optimum or desired gas compositions in another separate scan. For example, a scan may be performed to determine the elution times of the target ions or target molecules without varying the composition of the gas. The optimum or desired gas compositions may then be determined in a separate scan in which the gas composition is varied.

Alternatively, the pre-scan may comprise:

a) separating the target ions or target molecules in the first device according to said physicochemical property; and then b) separating or filtering the target ions according to their ion mobility in the ion mobility separation or filter device; and then c) detecting the target ions to provide a detection signal;

d) repeatedly performing steps a) to c), wherein the gas composition in the ion mobility separation or filter device is different for each time that step b) is repeated; and e) determining the optimum or desired gas composition for each target ion as the gas composition that provides the optimum or desired signal for that target ion from the detection signals detected in step c). For example, the gas composition that provides the best resolution in step c) for a target ion may be determined to be the optimum or desired gas composition for that target ion.

Step c) may also determine

Said elution times of the plurality of target ions or the plurality of molecules may be determined from step c).

The ion mobility separation or filter device may be supplied with a blend of gases comprising one or more gases selected from the group consisting of: a polar gas, an inert gas, a reactive gas, and a gas containing one or more volatile organic modifiers. Any combination of any two or more of the gases listed may be provided in the blend. For the avoidance of doubt, a reactive gas is a gas that may react with analyte ions within the ion mobility separation device.

The control system may be configured to monitor the drift time of a reference ion through the ion mobility separation or filter device and to adjust the gas composition within the ion mobility separation or filter device if the drift time of the reference ion through the gas composition differs from the expected drift time of the reference ion through that gas composition.

A reference ion may be used in order to ensure that the gas composition is controlled or varied in a consistent or reproducible manner between different experiments or separations. For instance, in addition to varying the gas composition as a function of time in the manner described above, the gas composition may be further adjusted based on the monitoring of the reference ion so as to correct for flow or temperature errors between different experiments or separations. A reference curve of drift time against gas composition or time may be produced for the reference ion, for example, by running a gas composition control program whilst monitoring the reference compound.

The control system may be configured to adjust said gas supply so as to change the composition of gas within the ion mobility separation or filter device as a function of time during a single experimental run.

Ions or molecules may be separated in the first device over a first time period and the composition of gas within said ion mobility separation or filter device may be changed during said first time period.

During the course of ions or molecules being separated in the first device there may essentially be a continuous flow of ions into the ion mobility separation or filter device.

The control system may be configured to control a device that changes the conformation of ions passing into or through said ion mobility separation or filter device as a function of time.

The conformation of ions may be changed by increasing their internal energy so that they unfold or partially unfold. The conformation of the ions may be changed by introducing energy to the ions passing into or through said ion mobility separation or filter device using photons, for example from a laser or other suitable light source. The conformation of ions may also be changed by collisionally induced activation, for example by accelerating the ions within a collision gas using a DC or AC field. A chemical reaction between the ions and a gas may also be used to change their conformation.

Said first device may be a chromatograph for separating molecules according to retention time and said control system may be configured to change the composition of gas within said ion mobility separation or filter device multiple times for multiple analytes having different retention times.

According to the first aspect, the present invention provides a method of mass spectrometry or ion mobility spectrometry comprising:

separating ions or molecules in a first device;

receiving in an ion mobility separation or filter device and separating or filtering according to their ion mobility at least some of said ions or ions derived from said molecules; and changing the composition of gas within said ion mobility separation or filter device as a function of time.

The ion mobility separation or filter device separates or filters ions transmitted by the first device, or ions derived from molecules transmitted by the first device.

The method may further comprise, prior to analysing a sample containing one or more target analytes, determining optimal conditions for ion mobility separation or filtering for ions of said target analytes and changing the composition of gas within said ion mobility separation or filter device as a function of time according to the determined optimal conditions.

The method may comprise performing a pre-scan that comprises analysing a sample comprising a plurality of target analyte ions so as to determine the optimum or desired gas composition for separating or filtering the target ions in said ion mobility separation or filtering device, wherein the different target ions are determined to have different optimum or desired gas compositions; subsequently supplying a sample comprising said target ions to said ion mobility or filter device and performing said step of separating or filtering said ions according to their ion mobility; wherein the gas supply is controlled such that whilst a first target ion is entering and/or separating in the ion mobility separation or filtering device the optimum or desired gas composition for the first target ion is present within the device, and whilst a second target ion is entering and/or separating in the ion mobility separation or filtering device the optimum or desired gas composition for the second target ion is present within the device.

The method may comprise:

performing a pre-scan comprising determining the elution times from the first device of a plurality of target ions, or determining the elution times from the first device of a plurality of molecules from which target ions are generated and then ionising the molecules to form target ions, and b) determining different optimum or desired gas compositions for separating or filtering different ones of the target ions in said ion mobility separation or filtering device; and then supplying a sample to said first device and performing said step of separating ions or molecules according to said physicochemical property and said step of separating or filtering said ions according to their ion mobility; wherein the gas composition in the ion mobility separation or filter device is varied as a function of elution time from the first device such that at elution times corresponding to the elution times of the target ions, or corresponding to the elution times of the molecules from which the target ions are generated, the gas composition in the ion mobility separation or filter device has the respective optimum or desired gas compositions for those target ions.

Different target ions are determined to have different elution times and different optimum or desired gas compositions The pre-scan may comprise:

(i) separating or filtering the target ions according to their ion mobility in the ion mobility separation or filter device;

(ii) detecting the target ions to provide a detection signal;

(iii) repeatedly performing steps (i) to (ii), wherein the gas composition in the ion mobility separation or filter device is different for each time that step (i) is repeated; and (iv) determining the optimum or desired gas composition for each target ion as the gas composition that provides the optimum or desired signal for that target ion from the detection signals detected in step (ii).

For example, the gas composition that provides the best resolution in step (ii) for a target ion may be determined to be the optimum or desired gas composition for that target ion.

The pre-scan may comprise determining the elution times of the target ions or target molecules in one scan and determining the optimum or desired gas compositions in another separate scan. For example, a scan may be performed to determine the elution times of the target ions or target molecules without varying the composition of the gas. The optimum or desired gas compositions may then be determined in a separate scan in which the gas composition is varied.

Alternatively, the pre-scan may comprise:

a) separating the target ions or target molecules in the first device according to said physicochemical property; and then b) separating or filtering the target ions according to their ion mobility in the ion mobility separation or filter device; and then c) detecting the target ions to provide a detection signal;

d) repeatedly performing steps a) to c), wherein the gas composition in the ion mobility separation or filter device is different for each time that step b) is repeated; and e) determining the optimum or desired gas composition for each target ion as the gas composition that provides the optimum or desired signal for that target ion from the detection signals detected in step c). For example, the gas composition that provides the best resolution in step c) for a target ion may be determined to be the optimum or desired gas composition for that target ion.

Step c) may also determine

Said elution times of the plurality of target ions or the plurality of molecules may be determined from step c).

The method may comprise providing any of the components or devices described above or carrying out any of the steps performed by the control system described above.

The method may comprise varying the gas composition in the ion mobility separation or filter device dynamically as a function of the separation in the first device.

The method may comprise controlling the gas composition in the ion mobility separation or filter device based on the ions or molecules eluting from the first device and passing into the ion mobility separation or filter device so that the gas in the IMS device is controlled to be of a first composition whilst a first analyte ion is passing through the IMS device, and the gas in the IMS device is controlled to be of a second composition whilst a second, different analyte ion is passing through the IMS device.

The method may comprise providing a gas supply connected to the ion mobility separation or filter device and comprising a plurality of gas controllers each connected to a reservoir of a different type of gas and changing the composition of gas within the ion mobility separation or filter device by controlling the gas flow controllers.

The method may comprise separating ions or molecules in the first device according to chromatographic or electrophoretic retention time; mass or mass to charge ratio; ion mobility or differential ion mobility; or volatility.

The method may comprise adjusting the composition of gas in the ion mobility separation or filter device with time so as to enhance or optimise ion mobility separation for multiple target ions present in said ion mobility separation or filter device at different times.

The method may comprise monitoring the drift time of a reference ion through the ion mobility separation or filter device and adjusting the gas composition within the ion mobility separation or filter device if the drift time of the reference ion through the gas composition differs from the expected drift time of the reference ion through that gas composition.

The method may comprise changing the conformation of ions passing into or through said ion mobility separation device as a function of time.

When the first device is a chromatograph, the method may comprise separating molecules according to retention time and changing the composition of gas within the ion mobility separation or filter device multiple times for multiple analytes having different retention times.

The ions or molecules need not be separated in a first device upstream of the ion mobility separation or filter device.

It is contemplated herein that the composition of the gas within the ion mobility separation or filter device may be varied dynamically as a population of ions separates/filters and elutes from the device. In this technique, different species from the same ion population may separate and elute from the ion mobility separation or filter device under different conditions of IMS gas composition, thereby allowing the conditions for optimal IMS separation/filtering to be adjusted for different target ions within the same population of ions. This approach may be used, for example, to optimise ion mobility separation/filtering conditions for multiple target ions which co-elute from the chromatographic device at substantially the same time and subsequently are separated in time or filtered by the device. This method also facilitates optimisation of the ion mobility separation or filtering conditions for populations of ions which are introduced into the device without pre-separation.

Accordingly, from a second aspect the present invention provides a method of ion mobility spectrometry comprising:

receiving ions in an ion mobility separation or filter device;

driving ions of different ion mobility from an entrance of the device towards an exit of the device at different rates so as to separate or filter the ions according to their drift time along or through the device; and changing the composition of gas within said ion mobility separation or filter device as a function of time.

US 2013/0320205 relates to a FAIMS device and recognises that the gas composition may be varied as a function of the compensation voltage so as to optimise the analysis of some of the ions. However, US '205 does not relate to a drift time IMS device, and so does not recognise that the gas composition may be used to optimise the ion mobility measurement derived from the drift time.

The method of the second aspect may comprise determining the ion mobilities of the ions from their drift times through the ion mobility separation device.

The spectrometer or method may have any one or combination of optional features described in relation to the first aspect of the present invention, except that there need not necessarily be a first device upstream of the ion mobility separation or filter device.

The method may comprise analysing a sample comprising a plurality of target analyte ions so as to determine the optimum or desired gas composition for separating or filtering the target ions in said ion mobility separation or filtering device, wherein the different target ions are determined to have different optimum or desired gas compositions; subsequently supplying a sample comprising said target ions to said ion mobility or filter device and performing said step of driving ions of different ion mobility from an entrance of the device towards an exit of the device; wherein the gas composition is controlled such that whilst a first target ion is separating and/or eluting from the ion mobility separation or filtering device the optimum or desired gas composition for the first target ion is present within the device, and whilst a second target ion is separating and/or eluting from the ion mobility separation or filtering device the optimum or desired gas composition for the second target ion is present within the device.

The second aspect the present invention also provides an ion mobility spectrometer comprising:

an ion mobility separation or filter device;

a gas supply for supplying gas within said device; and a control system configured to:

drive ions of different ion mobility from an entrance of the device towards an exit of the device at different rates so as to separate or filter the ions according to their drift time along or through the device; and control the gas supply so as to change the composition of gas within said ion mobility separation or filter device as a function of time.

The spectrometer may have any of the optional features described in relation to the second aspect of the present invention.

It is contemplated that devices other than IMS devices may benefit from the present invention.

Accordingly, from a third aspect the present invention provides a mass spectrometer or ion mobility spectrometer comprising:

a first device for separating ions or molecules according to a physicochemical property;

a second device for receiving at least some of said separated ions or ions derived from said separated molecules;

a gas supply connected to said second device for supplying gas to said second device; and a control system configured to adjust said gas supply so as to change the composition of gas within the second device as a function of time.

The second device may comprise: (i) an ion guide; (ii) an ion trap; or (iii) a fragmentation or reaction device or cell; and/or said control system may be configured to adjust said gas composition so as to dynamically control an ion-neutral, ion-molecule or ion-ion interaction or reaction within said second device.

The spectrometer may comprise any one or combination of features described in relation to the first aspect of the present invention, except wherein the IMS device is replaced with said second device.

The third aspect of the present invention also provides a method of mass spectrometry or ion mobility spectrometry comprising:

separating ions or molecules in a first device;

receiving at least some of said separated ions or ions derived from said molecules in a second device; and changing the composition of gas within said second device as a function of time.

According to a fourth aspect, the present invention also provides a method of mass spectrometry comprising:

(a) chromatographically separating analytes prior to ionization;

(b) ionising analytes as they chromatographically elute in an ion source;

(c) passing the ions through an ion guiding or ion trapping region;

(d) dynamically altering the composition of the gas within the ion guide or ion trap during the chromatographic separation time to optimize the conditions for different target analytes.

The ion guide may be an IMS separation device, FAIMS device or DMS device.

The ion guide may have RF confinement.

The optimum gas conditions for a given target analyte may be determined prior to the experiment using analyte standards.

A mass separator may be placed downstream of the ion guide device. The ion guide may be a sub-ambient RF-confined IMS separation device.

According to a fourth aspect, the present invention provides a mass spectrometer or ion mobility spectrometer comprising:

a first device for separating ions or molecules according to a physicochemical property;

an ion mobility separation or filter device for receiving and separating or filtering at least some of said ions or ions derived from said molecules according to their ion mobility; and a control system configured to change the conformation of ions passing into or through the ion mobility separation or filter device as a function of time.

The conformation of the ions may be changed as a function of time so as to enhance or optimise the ion mobility separation or filtering of the ions within the ion mobility separation or filter device.

The conformation of each of a plurality of different ions may be changed so as to enhance or optimise the ion mobility separation or filtering of the ions within the ion mobility separation or filter device.

The conformation of ions may be changed by: increasing the internal energy of the ions so that they unfold or partially unfold; and/or introducing energy to the ions using photons; and/or collisionally induced activation of the ions; and/or chemically reacting the ions with other molecules or ions.

The spectrometer may further comprise a gas supply connected to said ion mobility separation or filter device for supplying gas to said ion mobility separation or filter device.

The fourth aspect of the present invention also provides a method of mass spectrometry or ion mobility spectrometry comprising:

separating ions or molecules in a first device;

receiving in an ion mobility separation or filter device and separating or filtering according to their ion mobility at least some of said ions or ions derived from said molecules; and changing the conformation of ions passing into or through the ion mobility separation or filter device as a function of time.

The spectrometer described herein may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

BRIEF DESCRIPTION OF THE DRAWINGS

Various embodiments of the present invention will now be described, by way of example only, and with reference to the accompanying drawing in which:

FIG. 1 schematically shows a mass spectrometer which can be used with embodiments of the present invention.

DETAILED DESCRIPTION OF EMBODIMENT

The nature or composition of the gas within an ion guide or trap will affect its interactions with ions passing through the device. For instance, the composition of the ion mobility separator (IMS) buffer gas can have a large effect on the relative drift times of different analyte ions. This is also true of differential mobility filters where differences in compensation voltage for different analytes are strongly dependent on buffer gas composition.

Generally, these effects depend on the electronic or chemical interaction of the gas with the analyte ions. For instance, polar, or polarizable, IMS drift gases or drift gas modifiers can be used to resolve ion species which otherwise due to insufficient IMS resolution or even identical ion mobility in an inert IMS gas would not be resolved.

Where a sample is provided to an IMS instrument through a liquid chromatograph ("LC"), the composition of the IMS gas may be adjusted in order to optimize IMS separation and thus optimize signal-to-noise and detection limits for a given analyte at a given retention time. However, the optimum conditions for one target analyte eluting at one retention time may be non-optimal for other target analytes present in the sample, potentially resulting in increased interferences and reduced detection limits for these species. By way of illustration, because nitrogen is less polarizable than carbon dioxide, for example, the separation conditions in an otherwise identical IMS device would be different when operated with these different gases for ions having different dipole moments or different electronic structures.

In conventional IMS devices the gas composition is static over the course of a chromatographic separation, and must be chosen as a compromise for multiple targeted analytes.

An embodiment of the invention will now be described with reference to the schematic IMS-mass spectrometer having an integrated gas manifold shown in FIG. 1. In this embodiment, the composition of the buffer gas in an IMS device 4 may be dynamically changed within the timescale of the chromatographic separation to optimize the conditions for IMS separation for multiple analytes eluting at different retention times.

In FIG. 1, an analyte-containing sample is passed through a chromatograph 1 into a mass spectrometer instrument. The analyte molecules are thus separated according to retention time before being passed to an ion source 2 that produces sample ions. The chromatograph 1 may for instance be a liquid chromatography device, a gas chromatography device, a supercritical fluid chromatography device, a capillary electrophoresis device, a size-exclusion chromatography device or other type of separation device.

It is not essential that the separation device is a chromatograph or that it is disposed upstream of the ion source 2. The skilled person will understand that ions may additionally, or alternatively, be separated downstream of the ion source 2 and that the ions may be separated according to any physicochemical property, such as mass, mass to charge ratio or ion mobility. Further examples of this are described below. The timescale for separation may typically be significantly longer than the transit time of ions through the IMS device 4 so that the conditions can be changed throughout the separation cycle.

In the embodiment of FIG. 1, the ions produced in the ion source 2 are initially passed through an ion guiding, trapping or filtering device 3. A population of these ions is then separated in a sub-atmospheric pressure IMS device 4 and mass analysed in a mass analyser 5, such as an orthogonal acceleration time-of-flight ("oaTOF") mass analyser. The IMS device 4 may be an ion guide with RF confinement, but this is not essential. In this embodiment there is an essentially continuous flow of ions through the IMS device 4 during the chromatographic separation.

The skilled person will understand that this geometry and the illustrated components are not limiting. For instance, the mass analyser 5 need not be an oaTOF mass analyser and any other suitable components may be disposed upstream or downstream of the IMS device 4.

The IMS device 4 is connected to an adjustable gas supply in the form of a gas manifold 8 containing two independently controlled flow controllers 9 connected to two gas cylinders 6, 7. By adjusting the output from the flow controllers 9, the gas manifold is operable to supply the IMS device 4 with a blend of gases from the gas cylinders 6, 7. It is noted that any suitable number of gas cylinders may be fed into the manifold 8. The output of the flow controllers 9 can either be sent directly to the IMS cell 4 or via a mixing chamber 10.

The output of the flow controllers 9 may be controlled by a computer 11 connected to both the gas controllers 9 and the chromatograph 1. The computer 11 can run a pre-determined gas composition control program that synchronously starts dynamically altering the composition of the gas within the IMS device 4 once a chromatographic separation is started.

It is important that the gas manifold system 8 and the control system 11 can rapidly and reproducibly adjust the gas composition within the IMS device 4 with a sufficient degree of control. For instance, they should be operable to reproducibly introduce one or both of the gases from gas cylinders 6, 7 in reproducible proportions over the course of multiple separate experiments. The relative proportions may be varied as a pre-determined function of time synchronized to the start of each chromatographic separation.

Many suitable rapid and flexible gas blending systems are commercially available, for example, the MCQ Gas Blender 100/200 series from MCR Gas Mixers, Irvine, Calif., USA. This mixer allows a minimum of 3 and up to 64 different gases (with multiple units linked by USB) to be controlled and blended with a flow rate of 0-200 sccm and a reproducibility of 1% or less over the entire range. The response time from changing set point is in the order 50 ms. Other commercially available systems based on mass flow controllers have settling times of between 0.5-2 seconds.

Alternatively, relatively simple control software may be written to achieve the same result for any appropriate mass flow controller fed with different input gases having a single output.

It is emphasized that the gas composition need not necessarily change progressively between different gases from the beginning to the end of the chromatographic elution, but may vary in proportion, as a function of retention time, such that the IMS separation of targeted analytes is optimized at each retention time.

The total gas pressure within the IMS cell 4 may vary during this process within reasonable bounds. The only requirement is that the pressure and gas composition is reproducible from one chromatographic separation to the next. If desired, the pressure in the IMS device 4 may however be kept fairly constant by adjusting the flow of the two controllers 9 based on the known partial pressures and pumping speeds of the gases.

The gases supplied to and/or blended in the IMS device 4 can be selected as desired for different operating conditions. For instance they may be polar, non-polar or inert. Typical gases that may be used include helium, argon, nitrogen, carbon dioxide, carbon monoxide, nitrous oxide, nitrogen dioxide, sulphur dioxide, hydrogen or methane. In other less preferred embodiments, reactive gases such as ammonia or deuterium may be used. When reactive gases are supplied to the IMS cell 4, reactions may occur in reactive sub groups from the reactive gas add or substitute to the ions. In this case, the cross section and/or the mass to charge value of particular analyte ions at different times can be changed during the chromatographic elution.

The approach may be extended to introducing different amounts of different volatile organic drift gas modifiers during the course of the chromatographic separation. In this case, a volatile organic modifier may be introduced into a controlled gas flow and the proportion of modifier to gas may be controlled by dynamically controlling the flow of modifier into the gas stream. This may be done using a fluid pumping system. In its simplest form a syringe pump may be used, with the flow of the pump controlled via a computer 11. The flow of gas may be simultaneously adjusted with the flow of modifier to maintain the pressure within the IMS device 4 within reasonable limits.

Varying the nature of the gas composition during the course of a separation in the manner described above allows the IMS separation conditions within the device 4 to be optimized for different analytes at different retention times. This can ensure the best separation of analytes from the matrix and improve detection limits and quantification.

The optimal or desired conditions at each retention time may be determined from prior calibration experiments. For instance, the required conditions may be determined by analysing standards of the target analytes under different conditions. Alternatively, a pre-scan may be performed during the chromatography in which the composition of the gas is rapidly changed over a pre-determined range in order to determine the best conditions i.e. gas composition for a subsequent scan. Depending on the speed of response of the gas blending system it may also be possible to implement data-dependent optimization for a given analyte.

In some embodiments, a lock mobility reference compound may be used during the IMS experiment. For instance, the drift time of the reference compound may be used to check that the composition of the gas is reproducible for each separation cycle. A reference curve of drift time against time or gas composition for the reference compound can be produced prior to a batch analysis by running the gas composition program while monitoring the reference compound. During subsequent runs the gas composition may be altered, for instance to account for any flow errors or temperature effects, by periodically monitoring the drift time of the reference compound, comparing it to the reference curve and adjusting the set point of the flow controllers 9 as necessary. Typically these adjustments will be relatively small. Fine control of the buffer gas composition can be achieved by a feedback mechanism between the flow controllers 9 and the measured drift time of the reference ion through the IMS device 4.

As mentioned above, the present invention is not limited to chromatographic separation techniques and any forms of separation other than or additional to chromatography may be employed upstream of the IMS device 4.

For example, the IMS gas composition in a low pressure FAIMS filter can be dynamically adjusted in synchronization with mass selective ejection of ions from an ion trap. In this case, the composition of the buffer gas may be altered based on the optimum mobility filtering conditions for target ions within each mass range.

Another example is an IMS separation device followed by a FAIMS device. In this case the composition of the IMS gas in each device may be simultaneously optimized for each targeted analyte. This may be used in combination with a downstream mass analyser such as a TOF mass spectrometer.

In a further example a heated solids probe may be used with the gas composition being changed over the distillation profile of the sample mixture.

The skilled person will also understand that the techniques for changing gas composition described above are not limited to IMS applications like that described above in relation to FIG. 1. The present invention also extends to atmospheric, sub-atmospheric and above-ambient pressure IMS, DMS and FAIMS systems.

Furthermore, the techniques of the present invention may advantageously be applied to non-mobility applications. For instance, the gas composition within an ion guide, ion trap, or fragmentation or reaction cell may be changed in a similar controlled or pre-programmed manner during the course of an upstream separation. In this way, the conditions for various gas-phase ion-molecule reactions or interactions can be optimized or the ion-molecule reactions controlled during a chromatographic separation for multiple target analytes eluting at different times. The techniques of the present invention may also be used to control gas-phase ion-ion interactions. For example, the introduction of a proton transfer reagent such as perfluro-1,3-dimethylcyclohexane can be controlled during a chromatographic run to allow the extent of proton transfer charge stripping to be adjusted for particular analytes as they chromatographically elute. As another example, the techniques described herein may be used with the methods described in WO 2013/171495 (GREEN). GREEN describes a method of ionizing or exciting a neutral gas within a reaction cell using vacuum ultraviolet radiation to cause ion-excited neutral or ion-ion reactions.

The skilled person will recognize that the techniques of the present invention may equally lend themselves to many other ion-molecule and ion-ion interactions.

In another less preferred example, the nature of the target gas for collisionally induced dissociation may be dynamically changed to optimize the fragmentation conditions for particular analytes.

As an alternative, or additionally to what is described above, the conformation of the target analyte ions may be altered during or prior to IMS separation to provide optimum separation. For similar reasons to those discussed above, changing the conformation of the ions may change the interaction between the analyte and the buffer gas and hence the nature of the separation.

The conformation of the gas-phase ions may be altered by introducing energy activation before or during IMS separation. For example, by increasing the internal energy of the ions, they can be caused to unfold or partially unfold. Suitable sources of energy may be photons from laser or other light sources. Collisionally induced activation of ions may be achieved by accelerating ions within a target collision gas by a DC or an AC field (RF heating). The conformation may also be changed by introducing reactive gases as described above.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer or ion mobility spectrometer comprising:
   a first device for separating ions or molecules according to a physicochemical property;

an ion mobility separation device for receiving and separating at least some of said ions, or ions derived from said molecules, according to their ion mobility;

wherein the ion mobility separation device is configured to drive ions of different ion mobility from an entrance of the device towards an exit of the device at different rates so as to separate ions according to their drift time through the device and such that ions of different mobility exit the device at different times;

a gas supply connected to said ion mobility separation device for supplying gas into said ion mobility separation device; and a control system configured to adjust said gas supply so as to vary the composition of gas within the ion mobility separation device dynamically and as a function of time based on the separation or elution time of ions or molecules in said first device, and wherein the gas composition in the ion mobility separation or filter device is controlled based on the ions or molecules eluting from the first device and passing into the ion mobility separation device so that the gas in the ion mobility separation device is controlled to be of a first composition whilst a first analyte ion is passing through the ion mobility separation device, and the gas in the ion mobility separation device is controlled to be of a second composition whilst a second, different analyte ion is passing through the ion mobility separation device.

2. A spectrometer as claimed in claim 1, wherein said gas supply comprises a plurality of gas flow controllers each connected to a reservoir of a different type of gas and wherein said control system is configured to control the gas flow controllers so as to change the composition of gas within the ion mobility separation device as a function of time.

3. A spectrometer as claimed in claim 1, wherein said first device separates ions or molecules according to:
(i) chromatographic or electrophoretic retention time;
(ii) mass or mass to charge ratio;
(iii) ion mobility or differential ion mobility; or
(iv) volatility.

4. A spectrometer as claimed in claim 1, wherein the control system is configured to adjust the composition of gas in the ion mobility separation device with time so as to enhance or optimise ion mobility separation for multiple predetermined target ions present in said ion mobility separation device at different times.

5. A spectrometer as claimed in claim 1, further comprising a control system configured to:
perform a pre-scan that: a) determines the elution times from the first device of a plurality of target ions, or determines the elution times from the first device of a plurality of molecules from which target ions are generated and then ionises the molecules to form target ions, and b) determines different optimum or desired gas compositions for separating different ones of the target ions in said ion mobility separation device; and then supply a sample to said first device and to perform said step of separating ions or molecules according to said physicochemical property and said step of separating said ions according to their ion mobility; and to vary the gas composition in the ion mobility separation device as a function of elution time from the first device such that at elution times corresponding to the elution times of the target ions, or corresponding to the elution times of the molecules from which the target ions are generated, the gas composition in the ion mobility separation device has the respective optimum or desired gas compositions for those target ions.

6. A spectrometer as claimed in claim 1, wherein said control system is configured to monitor the drift time of a reference ion through the ion mobility separation device and to adjust the gas composition within the ion mobility separation device if the drift time of the reference ion through the gas composition differs from the expected drift time of the reference ion through that gas composition.

7. A method of mass spectrometry or ion mobility spectrometry comprising:
providing the spectrometer of claim 1;
separating ions or molecules in the first device;
receiving in the ion mobility separation device and separating according to their drift time through the ion mobility separation device at least some of said ions or ions derived from said molecules, such that ions of different mobility exit the ion mobility separation device at different times; and
changing the composition of gas within said ion mobility separation device as a function of time.

8. The method of claim 7, comprising performing a pre-scan that comprises analysing a sample comprising a plurality of target analyte ions so as to determine the optimum or desired gas composition for separating the target ions in said ion mobility separation device, wherein the different target ions are determined to have different optimum or desired gas compositions;
subsequently supplying a sample comprising said target ions to said ion mobility device and performing said step of separating said ions according to their ion mobility;
wherein the gas supply is controlled such that whilst a first target ion is entering and/or separating in the ion mobility separation device the optimum or desired gas composition for the first target ion is present within the device, and whilst a second target ion is entering and/or separating in the ion mobility separation device the optimum or desired gas composition for the second target ion is present within the device.

9. The method of claim 7, comprising performing a pre-scan comprising determining the elution times from the first device of a plurality of target ions, or determining the elution times from the first device of a plurality of molecules from which target ions are generated and then ionising the molecules to form target ions, and b) determining different optimum or desired gas compositions for separating different ones of the target ions in said ion mobility separation device; and then
supplying a sample to said first device and performing said step of separating ions or molecules according to said physicochemical property and said step of separating said ions according to their ion mobility; wherein the gas composition in the ion mobility separation device is varied as a function of elution time from the first device such that at elution times corresponding to the elution times of the target ions, or corresponding to the elution times of the molecules from which the target ions are generated, the gas composition in the ion mobility separation device has the respective optimum or desired gas compositions for those target ions.

10. The method of claim 8, wherein the pre-scan comprises:
(i) separating the target ions according to their ion mobility in the ion mobility separation device;
(ii) detecting the target ions to provide a detection signal;

(iii) repeatedly performing steps (i) to (ii), wherein the gas composition in the ion mobility separation device is different for each time that step (i) is repeated; and (iv) determining the optimum or desired gas composition for each target ion as the gas composition that provides the optimum or desired signal for that target ion from the detection signals detected in step (ii).

11. The method of claim 7, wherein the composition of gas within the ion mobility separation device is changed as a function of time during a single experimental run, optionally such that ions that are separated according to said physicochemical property are received at the ion mobility separation device at different times and experience different gas compositions.

12. A spectrometer as claimed in claim 1, wherein the control system is configured to adjust or control said gas supply so as to change the composition of gas within the ion mobility separation device as a function of time during a single experimental run, optionally such that ions that are separated according to said physicochemical property are received at the ion mobility separation device at different times and experience different gas compositions.

* * * * *